US012746326B2

(12) United States Patent
Fischer et al.

(10) Patent No.: US 12,746,326 B2
(45) Date of Patent: Sep. 29, 2026

(54) SYSTEMS AND METHODS FOR CONTROLLING PULSE MODE PUMPING IN INFUSION SYSTEMS

(71) Applicants: Baxter International Inc., Deerfield, IL (US); Baxter Healthcare SA, Glattpark (CH)

(72) Inventors: Steven Ward Fischer, Gurnee, IL (US); Morris Wallace, Wimauma, FL (US); Ye Chen, Lake Forest, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 896 days.

(21) Appl. No.: 17/954,597

(22) Filed: Sep. 28, 2022

(65) Prior Publication Data

US 2023/0098092 A1 Mar. 30, 2023

Related U.S. Application Data

(60) Provisional application No. 63/249,302, filed on Sep. 28, 2021.

(51) Int. Cl.
*A61M 5/142* (2006.01)
*F04B 49/06* (2006.01)

(52) U.S. Cl.
CPC ........... *A61M 5/142* (2013.01); *F04B 49/065* (2013.01); *A61M 2005/14208* (2013.01); *F04B 2203/0202* (2013.01); *F04B 2203/0209* (2013.01)

(58) Field of Classification Search
CPC ........ A61M 2005/14208; A61M 5/142; A61M 5/145; A61M 5/1452; F04B 49/06; F04B 49/065; F04B 49/20

(Continued)

(56) References Cited

U.S. PATENT DOCUMENTS

2006/0198166 A1* 9/2006 Hirono .................... H02P 27/08 363/15
2013/0253419 A1 9/2013 Favreau (Continued)

FOREIGN PATENT DOCUMENTS

EP 0319267 A2 6/1989
WO 2009/039203 A2 3/2009

OTHER PUBLICATIONS

International Search Report from International Patent Application No. PCT/2022/045034, mailed Dec. 13, 2022.

*Primary Examiner* — Philip E Stimpert

(74) *Attorney, Agent, or Firm* — K&L Gates LLP

(57) ABSTRACT

The present disclosure provides a new and innovative method and system for flow rate compensation in devices, such as medical devices and other electronic devices. In various embodiments, a computer-implemented method includes dispensing, by a pump controlled by a controller, a fluid from a fluid supply in a pulse mode over a period by determining a pulse volume for a pulse, determining a pulse cycle time, and for the period: controlling the position of the pump to perform a delay and perform a pulse to dispense an amount of the fluid, the pulse performed for the pulse cycle time, calculating an overshoot or undershoot of the amount of the fluid dispensed relative to the pulse volume, adjusting the pulse cycle time based on the calculated overshoot or undershoot, and repeating the dispensing until the period has elapsed.

18 Claims, 14 Drawing Sheets

(58) Field of Classification Search
USPC ........................................................... 604/67
See application file for complete search history.

(56) References Cited

U.S. PATENT DOCUMENTS

2013/0303989 A1* 11/2013 Favreau .................... H02P 8/18
318/685
2014/0088554 A1* 3/2014 Li ..................... A61M 5/14248
604/67

* cited by examiner

700

720

740

800

820

900

940

SYSTEMS AND METHODS FOR CONTROLLING PULSE MODE PUMPING IN INFUSION SYSTEMS

PRIORITY CLAIM

This application claims priority to and the benefit as a non-provisional application of U.S. Provisional Patent Application No. 63/249,302, filed Sep. 28, 2021, the entire contents of which are hereby incorporated by reference and relied upon.

TECHNICAL FIELD

The instant application is directed towards medical pumps, and more specifically to control systems of medical pumps that provide pulse mode pumping for low flow rates.

BACKGROUND

The present disclosure provides new and innovative methods and systems for flow control in electronic devices, including medical devices. In various embodiments, the device includes an infusion pump. Generally, medical patients sometimes require precise delivery of either continuous medication or medication at set periodic intervals. Medical pumps provide controlled fluid drug infusion such that the drug can be administered at a precise rate that keeps a drug concentration within a therapeutic margin and out of an unnecessary or possibly toxic range. The medical pumps can provide appropriate drug delivery to patients at a controllable rate, which does not require frequent attention.

Medical pumps may facilitate administration of intravenous (IV) therapy to patients both in and outside of a clinical setting. Outside a clinical setting, doctors have found that in many instances patients can return to substantially normal lives, provided they receive periodic or continuous intravenous administration of medication. Among the types of therapies requiring this kind of administration are antibiotic therapy, chemotherapy, pain control therapy, nutritional therapy, and several other types known by those skilled in the art. In many cases, patients receive multiple daily therapies. Certain medical conditions require infusion of drugs in a solution over relatively short periods such as from thirty minutes to two hours. These conditions and others have combined to promote the development of increasingly lightweight, portable, or ambulatory infusion pumps that can be worn by a patient and are capable of administering a continuous supply of medication at a desired rate, or providing several doses of medication at scheduled intervals.

Configurations of infusion pumps include elastomeric pumps, which squeeze solution from flexible containers, such as balloons, into IV tubing for delivery to a patient. Alternatively, spring-loaded pumps pressurize solution containers or reservoirs. Certain pump designs utilize cartridges containing flexible compartments that are squeezed by pressure rollers for discharging the solutions. Infusion pumps utilizing syringes are also known where a drive mechanism moves a plunger of a syringe to deliver fluid to a patient. Typically, these infusion pumps include a housing adapted to receive a syringe assembly, a drive mechanism adapted to move the syringe plunger, a pump control unit having a variety of operating controls, and a power source for powering the pump including the drive mechanism and controls.

Additionally, some infusion pumps are portable. For instance, an infusion pump may be smaller and more compact for mobile use by ambulatory patients or other patients. Naturally, a portable pump must be supplied with an equally portable power source as a means for powering the pump motor. Batteries are a suitable choice of power for portable units. Some pumps may use disposable batteries while other pumps may use rechargeable batteries. The pump may also be sized to be attached to an IV pole. The IV pole, with attached pump, may remain stationary or may be moved about in a hospital setting. In another example, the pump may be attached to a hospital bed or other support structure. As noted above, the pump may be portable and may be carried on the patient, for instance, in a pouch. The pump may be attached to and supported by the patient's clothing and/or other support apparel such as a belt, a vest, or the like.

Several methods exist to ensure that a medical device deliver medication at a specified rate. However, the existing methods have several disadvantages, limitations, and drawbacks. For example, existing methods utilize a motor-powered pump to deliver medication, where the operation of the motor is used to control the operation of the pump. This can be particularly problematic when the motor is operating in a low power mode. In these instances, if the positional control of the motor is inaccurate or unreliable, the medical device may stop functioning and/or fail to deliver medication at a specified rate. Accordingly, a method and system for controlling the operation of pumps and managing the flow rate of medical devices that does not require user intervention is desired.

SUMMARY

The present disclosure provides new and innovative methods and systems for flow rate compensation in devices, such as medical devices and other electronic devices. The flow rate compensation discussed herein enables medical devices to automatically maintain flow rates within a desired flow rate accuracy threshold with little or no user intervention. The flow rate compensation is provided during a pulse mode operation, when a pump motor typically operates at a slower rate by turning on for short durations of time. The flow rate compensation is based on consistent and accurate control of pump motor movement, taking a target travel delta or a final position as an input. This final position is compared to the expected position of the motor and/or pump after the pulse is performed.

Tracking the pumping cycle position allows for compensation to be applied, which increases or decreases a pulse duration relative to the starting position of the movement. The control of the movement speed during a positional movement is generally limited since the control point is a distance from a target versus a velocity of movement. While operating in pulse mode, the power consumed by the pump is reduced by placing the pump electrical components (e.g., motor control circuitry, display circuitry, safety circuits, computational components, and the like) into a low power state during the off periods of the pulse mode cycle. This results in a system that is both more economically efficient and improves the ability of the system to deliver treatments to patients.

In light of the disclosure set forth herein, and without limiting the disclosure in any way, in a first aspect of the present disclosure, which may be combined with any other aspect, or portion thereof, described herein a computer-implemented method includes dispensing, by a pump controlled by a controller, a fluid from a fluid supply in a pulse mode over a period by determining a pulse volume for a pulse, determining a pulse cycle time, and for the period: controlling the position of the pump to perform a delay and perform a pulse to dispense an amount of the fluid, the pulse performed for the pulse cycle time, calculating an overshoot or undershoot of the amount of the fluid dispensed relative to the pulse volume, adjusting the pulse cycle time based on the calculated overshoot or undershoot, and repeating the dispensing until the period has elapsed.

In a second aspect of the present disclosure, which may be combined with any other aspect, or portion thereof, described herein the fluid supply comprises an IV bag.

In a third aspect of the present disclosure, which may be combined with any other aspect, or portion thereof, described herein the overshoot or undershoot is calculated based on measuring the position of the pump prior to and after the pulse.

In a fourth aspect of the present disclosure, which may be combined with any other aspect, or portion thereof, described herein the method further includes controlling a voltage level of the pulse by starting, via the controller, a timer, after an elapsed time, reading, via the controller, an encoder position of a motor of the pump, comparing, via the controller, the encoder position of the motor to a target position, when the encoder position is equal to or greater than the target position, maintain, via the controller, a voltage level of the pulse, and when the encoder position is less than the target position, subtracting, via the controller, the encoder position from the target position and use the difference to increase the voltage level of the pulse.

In a fifth aspect of the present disclosure, which may be combined with any other aspect, or portion thereof, described herein the voltage level of the pulse is increased by adjusting, via the controller, the difference between the encoder position and the target position using at least one PID operating parameter, calculating, via the controller, a pulse width modulation (PWM) voltage using the adjusted difference, and increasing, via the controller, the voltage level of the pulse based on the calculated PWM voltage.

In a sixth aspect of the present disclosure, which may be combined with any other aspect, or portion thereof, described herein the at least one PID operating parameter includes Kp, Ki, and Kd for the controller.

In a seventh aspect of the present disclosure, which may be combined with any other aspect, or portion thereof, described herein the method further includes comparing, via the controller, the PWM voltage to a voltage limit, and when the voltage limit is exceeded, reducing, via the controller, the PWM voltage to the voltage limit.

In an eighth aspect of the present disclosure, which may be combined with any other aspect, or portion thereof, described herein the method further includes comparing, via the controller, the PWM voltage to a minimum motor speed, and when the minimum motor speed is below a threshold, increasing, via the controller, the PWM voltage to at least the threshold.

In a ninth aspect of the present disclosure, which may be combined with any other aspect, or portion thereof, described herein the pulse volume for the pulse is determined based on a volume of the fluid to be delivered.

In a tenth aspect of the present disclosure, which may be combined with any other aspect, or portion thereof, described herein the pulse cycle time is determined based on at least one of a volume of the fluid to be delivered or a time period associated with the infusion treatment.

In an eleventh aspect of the present disclosure, which may be combined with any other aspect, or portion thereof, described herein the method further includes after the period reading, via the controller, an encoder position of a motor of the pump, comparing, via the controller, the encoder position of the motor to a target position, when the encoder position is greater than the target position, subtracting, via the controller, a difference between the target position and the encoder position from a position of a next pulse for a next period, and when the encoder position is less than the target position, adding, via the controller a difference between the encoder position and the target position to a position of a next pulse for a next period.

In a twelfth aspect of the present disclosure, which may be combined with any other aspect, or portion thereof, described herein an infusion pump apparatus includes a pump motor configured to pump fluid through intravenous tubing and a controller configured to control the pump motor to perform an infusion treatment. The controller is configured to cause the fluid to be dispensed in a pulse mode over a period by determining a pulse volume for a pulse, determining a pulse cycle time, and for the period controlling a position of the pump motor to perform a delay, and perform a pulse to dispense an amount of the fluid, the pulse performed for the pulse cycle time. The controller is also configured to calculate an overshoot or undershoot of the amount of the fluid dispensed relative to the pulse volume, adjust the pulse cycle time based on the calculated overshoot or undershoot, and repeat the dispensing until the period has elapsed.

In a thirteenth aspect of the present disclosure, which may be combined with any other aspect, or portion thereof, described herein the controller comprises a proportional, integral, derivative (PID) controller.

In a fourteenth aspect of the present disclosure, which may be combined with any other aspect, or portion thereof, described herein the overshoot or undershoot is calculated based on measuring the position of the pump motor prior to and after the pulse.

In a fifteenth aspect of the present disclosure, which may be combined with any other aspect, or portion thereof, described herein the controller further controls a voltage level of the pulse by starting a timer, after an elapsed time, reading an encoder position of the pump motor, comparing the encoder position of the pump motor to a target position, when the encoder position is equal to or greater than the target position, maintain a voltage level of the pulse, and when the encoder position is less than the target position, subtracting, the encoder position from the target position and use the difference to increase the voltage level of the pulse.

In a sixteenth aspect of the present disclosure, which may be combined with any other aspect, or portion thereof, described herein the voltage level of the pulse is increased by adjusting the difference between the encoder position and the target position using at least one PID operating parameter, calculating a pulse width modulation (PWM) voltage using the adjusted difference, and increasing the voltage level of the pulse based on the calculated PWM voltage.

In a seventeenth aspect of the present disclosure, which may be combined with any other aspect, or portion thereof, described herein the at least one PID operating parameter includes Kp, Ki, and Kd for the controller.

In an eighteenth aspect of the present disclosure, which may be combined with any other aspect, or portion thereof, described herein the controller is further configured to compare the PWM voltage to a voltage limit, and when the voltage limit is exceeded, reduce the PWM voltage to the voltage limit.

In a nineteenth aspect of the present disclosure, which may be combined with any other aspect, or portion thereof, described herein the controller is configured to enter the pulse mode based on a specified type or a specified fluid infusion rate of the infusion treatment.

In a twentieth aspect of the present disclosure, which may be combined with any other aspect, or portion thereof, described herein the controller is further configured to after the pulse, read an encoder position of the pump motor, compare the encoder position of the pump motor to a target position, when the encoder position is greater than the target position, subtract a difference between the target position and the encoder position from a position of a next pulse for a next period, and when the encoder position is less than the target position, add a difference between the encoder position and the target position to a position of a next pulse for a next period.

In a twenty-first aspect, any of the features, functionality and alternatives described in connection with any one or more of FIGS. 1 to 9C may be combined with any of the features, functionality and alternatives described in connection with any other of FIGS. 1 to 9C.

In light of the present disclosure and the above aspects, it is therefore an advantage of the present disclosure to provide flow rate compensation for infusion pumps.

It is another advantage of the present disclosure to provide precise fluid volume control for a pulse pumping mode of an infusion pump.

Additional features and advantages of the disclosed method and apparatus are described in, and will be apparent from, the following Detailed Description and the Drawings. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

The description will be more fully understood with reference to the following figures, which are presented as exemplary aspects of the disclosure and should not be construed as a complete recitation of the scope of the disclosure.

DETAILED DESCRIPTION

Figure 1:
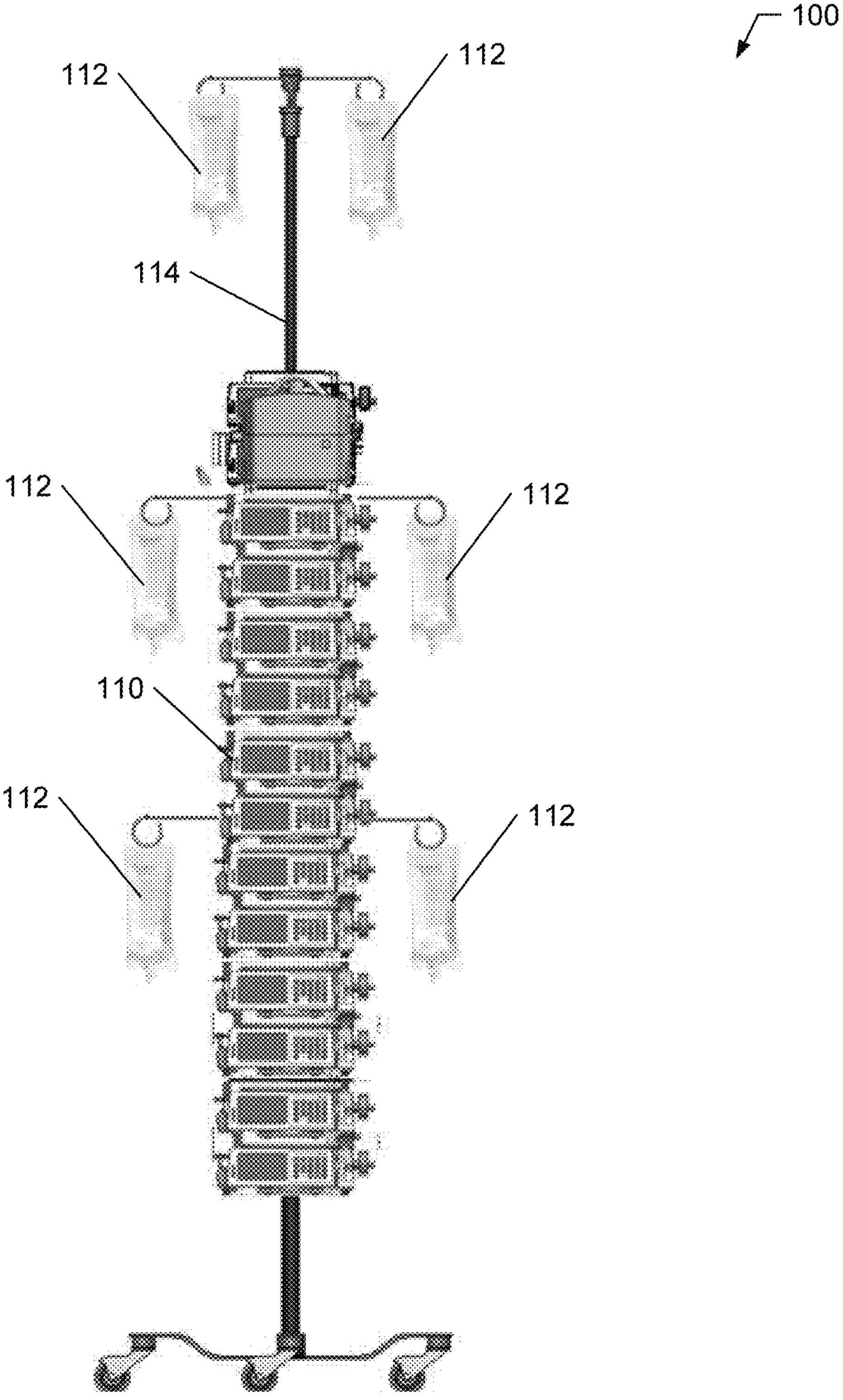
FIG. 1 illustrates a diagram of a device stack, according to an example aspect of the present disclosure.

Turning now to the drawings, techniques are disclosed for new and innovative systems and methods for flow rate compensation in devices, such as medical devices and other electronic devices. A variety of devices, such as infusion pumps, can be used to deliver treatments to patients. These treatments typically include delivering medication at a particular flow rate. The infusion pumps are commonly installed on a mobile IV stand, with one or more IV bags hung from a top of the mobile IV stand and one or more infusion pumps mounted to a pole in a middle of the mobile IV stand. Infusion pumps typically have two modes of operation, a high flow rate mode and a low flow rate mode. During the high flow rate mode (e.g., a non-pulsed mode), infusion pumps deliver accurate flow rates of a fluid by moving a pumping mechanism at a controlled speed or velocity. When running at low flow rates, in order to maximize battery run-time, the pump operates in a low power intermittent operation. When in the low flow rate mode (e.g., the pulse mode), a controller is configured to pulse the pumping mechanism for short durations with an off time between each pulse. The overall flow rate is determined by measuring a volume of fluid delivered during each pulse and an amount of time between the pulses.

Existing control techniques emphasize accurate control of the pumping mechanism speed, taking a target speed as an input. Velocity control typically does not have consistent and accurate position control unless the speed is significantly reduced. A reduction in speed results in long pulse movement time and additional battery power consumption for each pulse movement. These velocity-controlled pumping mechanisms can be difficult to operate to minimize any error in the dispensed volume of fluid relative to the intended volume of fluid for each pulse. Hence, a more effective mechanism is needed to minimize the accumulation of these per pulse errors throughout the infusion. Systems and methods in accordance with aspects of the disclosure are capable of obtaining accurate positional control of the pumping mechanism and/or compensating for errors in the pump and/or motor operation, particularly during pulse mode operation. These techniques can reduce the amount of power needed to generate the pulses, limiting the infusion speed during a pulse, and achieving more accurate flow rates as compared to typical infusion pumps.

The pumping system of the infusion pump is configured to pulse a pumping mechanism for short durations with an off time between each pulse. Each individual pulsing operation can introduce flow rate accuracy error. Infusion pumps in accordance with aspects of the disclosure are configured to use a closed loop direct current (DC) motor driven rotational cam pumping mechanism and a position control proportional, integral, derivative (PID) controller for operating the pumping mechanism. PID controllers are preferred due to their consistency and accuracy of end position determination. However, it should be noted that any controller can be used in accordance with aspects of the disclosure. An additional objective, particularly with battery-powered devices, is to minimize the amount of power consumed while pumping. During a pulse mode infusion, devices in accordance with aspects of the disclosure are configured to enter a sleep mode when not actively infusing or interacting with a user. Therefore, the amount of power needed to perform pumping during each pulse is optimized to improve power consumption and ensure patient safety.

Systems and methods in accordance with aspects of the disclosure improve on existing techniques and can automatically maintain flow rates within a desired flow rate accuracy threshold with little or no user intervention. Infusion pumps (and any other devices) in accordance with aspects of the disclosure provide an improved pulse mode operation that improves the accuracy of fluid delivery in a pulse mode along with improved energy efficiency. In many aspects, the infusion pumps measure an ending position of a motor and/or pump after a pulse. This positional control methodology emphasizes consistent and accurate control of movement, taking a target travel delta or a final position as an input. This final position can be compared to the expected position of the motor and/or pump after the pulse is performed. Each pulse is intended to output the same volume of fluid to maintain a continuity of fluid flow. However, pumping mechanisms typically do not output a constant volume of fluid during the pumping cycle. As a result of this pumping inconsistency, an amount of fluid output often varies according to the pumping cycle position. Tracking the pumping cycle position allows for compensation to be applied, which increases or decreases the pulse duration relative to the starting position of the movement. The control of the movement speed during a positional movement is generally limited, typically just a maximum voltage limit, since the control point is a distance from a target versus a velocity of movement. In many aspects, it may be possible to perform reverse movements of the pumping mechanisms to correct positional overshoots. While operating in pulse mode, the power consumed by the pump is reduced by putting the pump electrical components (e.g., motor control circuitry, display circuitry, safety circuits, computational components, and the like) into a low power state during the off periods of the pulse mode cycle. This results in a system that is both more economically efficient and improves the ability of the system to deliver treatments to patients.

A variety of systems and processes in accordance with aspects of the disclosure are described in more detail below.

Systems and Devices

FIG. 1 illustrates a diagram of a device stack 100, according to an example aspect of the present disclosure. The device stack 100 includes one or more devices (e.g., infusion pumps) 110 and one or more fluid supplies (e.g., IV bags) 112 mounted to a mounting device (e.g., an IV pole) 114. The devices 110 can include one or more infusion pumps or any other electronic devices as appropriate. The devices 110 are configured to be programmed to receive fluid from the fluid supplies 112 and dispense the fluid at a specified rate using a variety of processes, as described herein.

Figure 2:
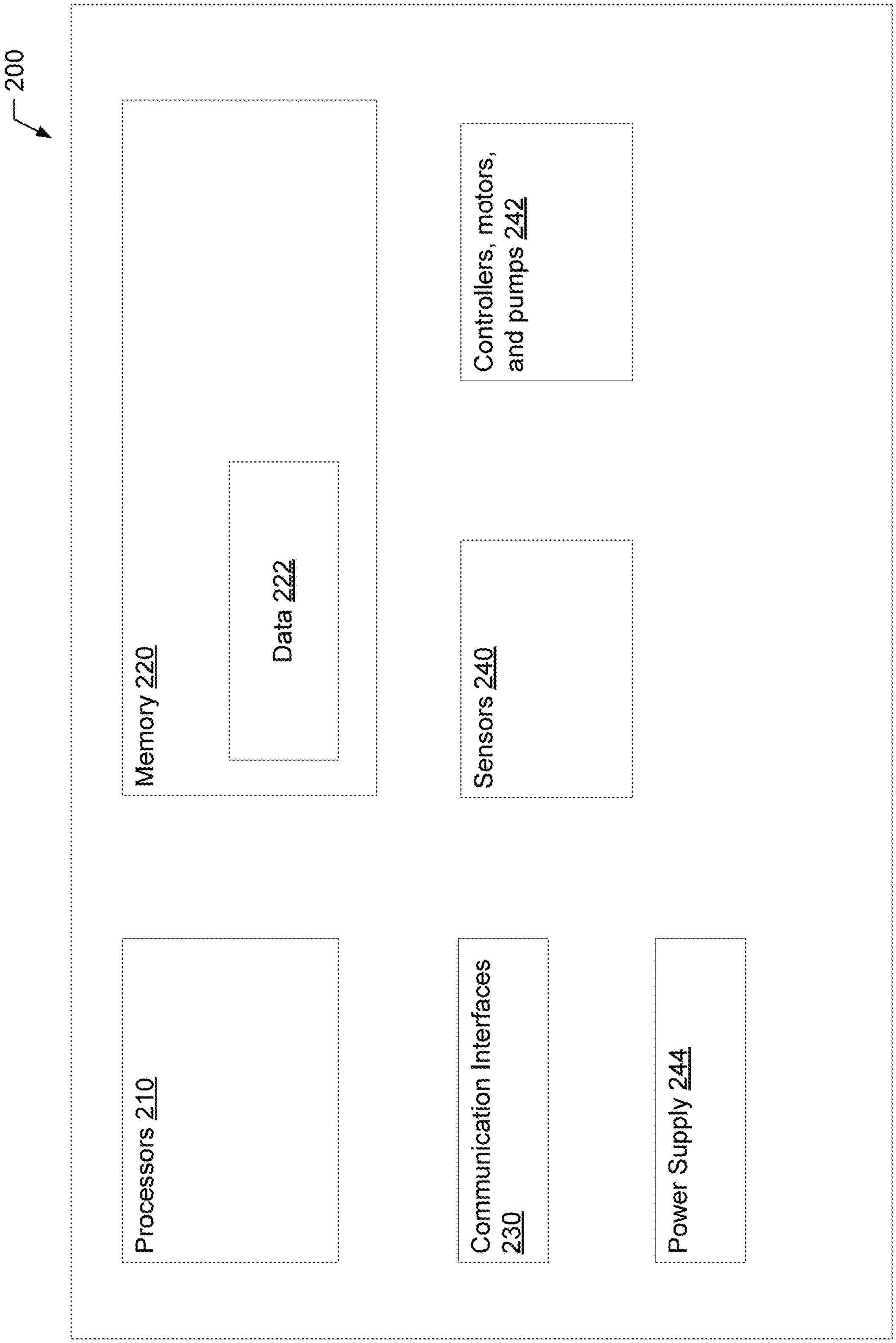
FIG. 2 illustrates a block diagram of an electronic device, according to an example aspect of the present disclosure.

FIG. 2 illustrates a block diagram of an electronic device 200, according to an example aspect of the present disclosure. The device 200 includes one or more processors 210, a memory 220, communication interfaces 230, sensors 240, controllers, motors, and pumps 242, and/or a power supply 244. The processor 210 may also be referred to as a central processing unit (CPU). The processor 210 can include one or more devices configured to execute instructions encoding arithmetic, logical, and/or I/O operations. In many aspects, the processor 210 may be a single core processor that is typically capable of executing one instruction at a time (or process a single pipeline of instructions) and/or a multi-core processor that may simultaneously execute multiple instructions. In a variety of aspects, the processor 210 may be implemented as a single integrated circuit, two or more integrated circuits, and/or may be a component of a multi-chip module in which individual microprocessor dies are included in a single integrated circuit package and hence share a single socket.

The memory 220 can include any combination of volatile and/or non-volatile memory devices, such as RAM, ROM, EEPROM, or any other device capable of storing data. In a number of embodiments, the memory 220 stores a variety of data 222. In a variety of embodiments, the data 222 causes the device 200 to perform any of a variety of processes, as described herein.

The communication interfaces 230 can include a network device (e.g., a network adapter or any other component that connects a computer to a computer network), a peripheral component interconnect (PCI) device, storage devices, disk drives, sound or video adaptors, photo/video cameras, printer devices, keyboards, displays, etc. The communications interfaces 230 can communicate via a variety of networks as appropriate. These networks can include a LAN (local area network), a WAN (wide area network), a telephone network (e.g., Public Switched Telephone Network (PSTN)), a Session Initiation Protocol (SIP) network, a wireless network, a point-to-point network, a star network, a token ring network, a hub network, wireless networks (including protocols such as EDGE, 3G, 4G LTE, Wi-Fi, 5G, WiMAX, and the like), the Internet, and the like. A variety of authorization and authentication techniques, such as username/password, Open Authorization (OAuth), Kerberos, SecureID, digital certificates, and more, may be used to secure the communications.

The sensor devices 240 can include a variety of sensors to sense a variety of environmental and/or physical conditions. In several embodiments, the sensor devices 240 can be used to measure and/or record data regarding a patient being treated for a particular condition. In a variety of embodiments, the sensor devices 240 are configured to measure a motor position, a pump position, a voltage, a battery level, a fluid flow, and/or any other data as described herein. The controllers, pumps, and motors 242 can include any devices used to perform actions, such as electronic components, microcontrollers (such as PID controllers) motors, pumps, actuators, and the like. These actions can include, but are not limited to, adjusting an electrical output of a device, pumping fluid provided by a fluid supply, regulating a delivery of medicine (particularly within a desired flow rate accuracy), and the like. In a variety of aspects, the motor and pump are separate components. In many aspects, the motor and pump are a single component. In a number of aspects, some or all of the controllers, motors, and pumps 242 are implemented using the one or more processors 210.

The power supply 244 is configured to provide power to any of the components of the device 200. The power supply 244 can include batteries, capacitors, transformers, charging circuitry, and/or any other device capable of providing AC and/or DC power to the components of device 200. In a variety of embodiments, the power supply 244 includes an AC/DC converter that converts AC power into 3.3V, 5V, and/or 12V DC power for the components of the device 200. Charging circuitry of the power supply 244 can include any suitable charger, such as an AC charger, a DC charger, solar panels, energy harvesters, and the like.

Although specific architectures for electronic devices in accordance with embodiments of the invention are illustrated in FIG. 2, any of a variety of architectures, including those that store data or applications on a disk or some other form of storage and are loaded into a memory at runtime, can also be utilized. Additionally, any of the data utilized in the system can be cached and transmitted once a network connection (such as a wireless network connection via the communications interface) becomes available. In a variety of embodiments, a memory includes circuitry such as, but not limited to, memory cells constructed using transistors, that store instructions. Similarly, a processor can include logic gates formed from transistors (or any other device) that dynamically perform actions based on the instructions stored in the memory. In several embodiments, the instructions are embodied in a configuration of logic gates within the processor to implement and/or perform actions described by the instructions. In this way, the systems and methods described herein can be performed utilizing both general-purpose computing hardware and by single-purpose devices.

Device Operation Processes

As described herein, it is desirable for infusion pumps (and a variety of electronic devices) to accurately dispense fluid at a particular flow rate within a desired flow rate accuracy. In a variety of aspects, the infusion pump is programmed to deliver a fluid flow at a particular rate based on a fluid supply. The infusion pump is configured to use a controller, such as a PID controller, to accurately determine the operation of a motor and/or pump and dynamically correct for errors in the operation of the pump, particularly in pulse mode operation.

Figure 3:
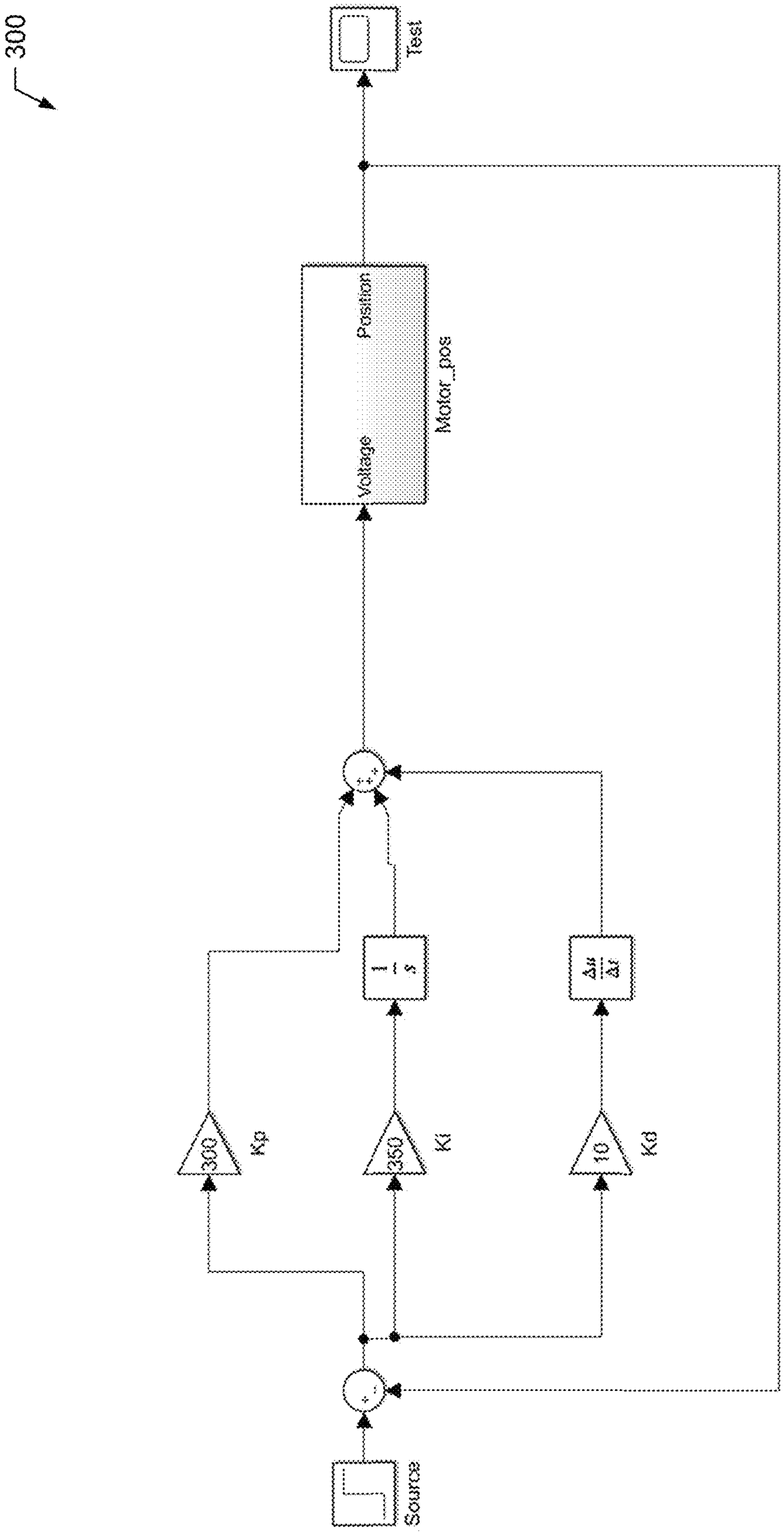
FIG. 3 is a diagram of a controller for a motor and/or pump, according to an example aspect of the present disclosure.

FIG. 3 is a diagram of a PID controller 300 for a motor and/or pump, according to an example aspect of the present disclosure. The controller PID 300 may include the controller 242 of FIG. 2. The PID controller 300 is configured to control the operation of a motor and/or pump with consistency and accuracy of an end position. As shown in FIG. 3, during each pulse, the motor and/or pump can have a varying amount of travel due to the non-linear delivery of the components. The PID controller 300 is configured to monitor the position of the motor and/or pump before and after each pumping pulse. In several aspects, the PID controller 300 controls the speed (e.g. velocity) of the pump and/or motor during the operation of the pump and/or motor. The PID controller 300 can ramp the speed when starting the operation of the pump and/or motor. This can be done to limit the current draw spike of the motor when transitioning from a stopped state to a moving state at or near a desired speed. After the motor has reached the desired speed, a floating voltage limit can be applied. This initial floating voltage limit can be derived based on the operation of the pump and/or motor under typical loading. After the initial floating voltage limit is determined, the speed can be continually monitored and when the speed drops significantly, such as due to load torque variations, the floating voltage limit can be increased to try to maintain the desire speed. As the PID controller 300 closes in on the target operation of the pump and/or motor as determined based on the PID operating parameters $K_p$, $K_i$, and $K_d$, the voltage can drop away from the floating limit due to the PID operating parameters being recalculated based on the position error to the target. In several aspects, the floating voltage limit does not affect the proper behavior of the PID controller; rather, it applies a limit to keep the infusion speed close to the target speed.

When an infusion pump is operating in a pulse mode, each time a pulse movement ends there is the possibility of a position error. These errors can accumulate over all the pulses in an infusion and result in a significant error at the end of the infusion. This error can affect the amount of fluid dispensed to a patient. In order to prevent these errors from accumulating, an approach is taken such that the error in the previous pulse is included in the movement of the next pulse. In many aspects, the next pulse movement is calculated assuming there was no error in the last movement in order to prevent cumulative errors due to the linearization of the mechanism movement. After the new pulse is calculated based on the previous target position, the previous positional error can be added (when the previous movement was short) or subtracted (when the previous movement was long) to the next pulse movement. By controlling the operation of the pump and/or motor in this way, errors occurring during the pulse mode operation do not accumulate, with the final pulse movement error being the only remaining error when the infusion process ends. The infusion process can end after a specified period of time, after amount of fluid has been delivered, and/or any other criteria as appropriate.

Figure 4:
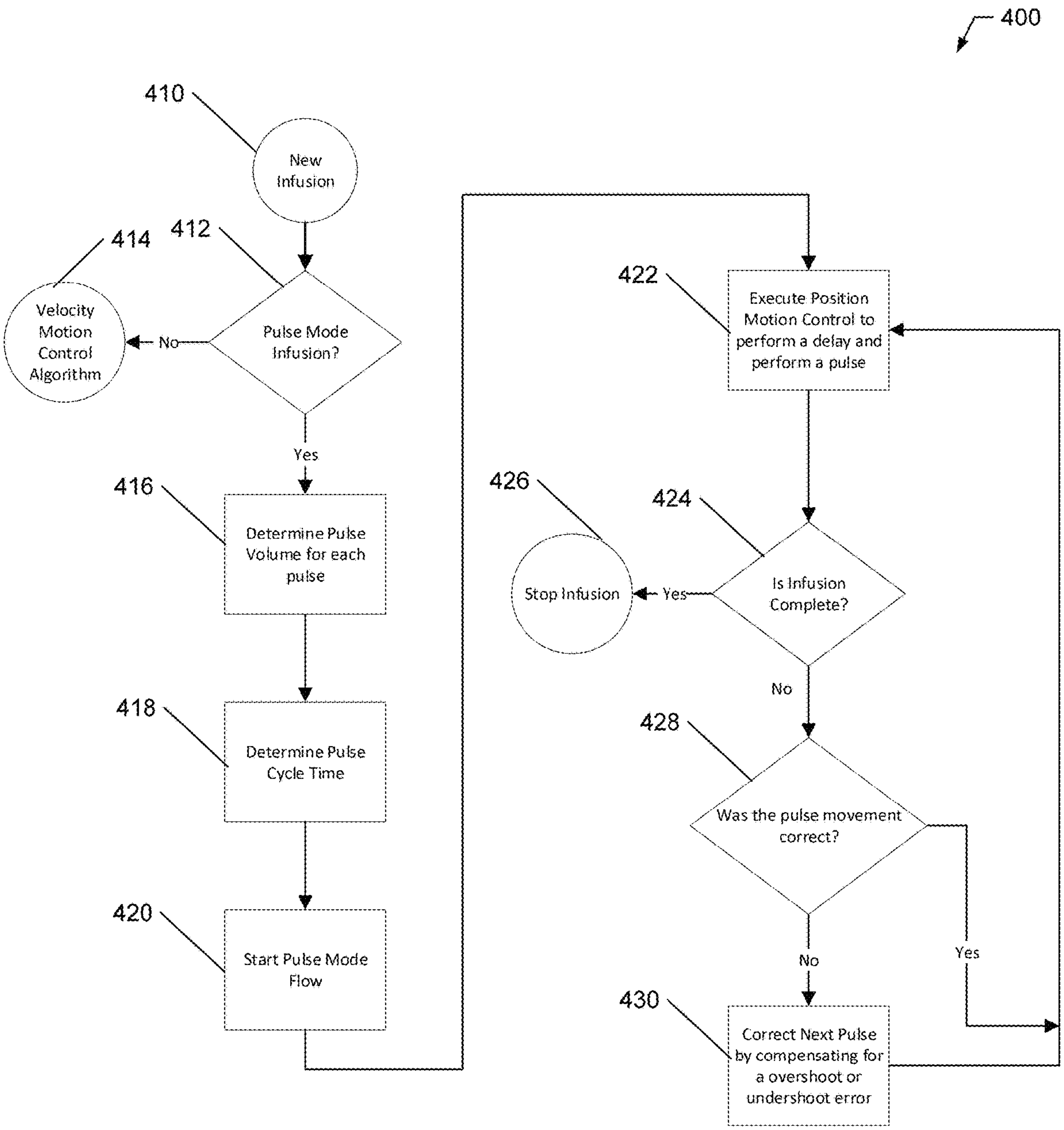
FIG. 4 illustrates a flowchart of a pulse mode operation process, according to an example aspect of the present disclosure.

FIG. 4 illustrates a flowchart of a pulse mode operation 400, process according to an example aspect of the present disclosure. Although the process 400 is described with reference to the flowchart illustrated in FIG. 4, it should be appreciated that many other methods of performing the acts associated with the process 400 may be used. For example, the order of some of the blocks may be changed, certain blocks may be combined with other blocks, one or more blocks may be repeated, and some of the blocks described are optional. The process 400 may be performed by processing logic that may include hardware (circuitry, dedicated logic, etc.), software, or a combination of both. In a variety of aspects, pulse mode operation processes can be performed by a controller operating a motor and/or pump within an infusion pump device.

As shown in FIG. 4, a new infusion can be started (410). The infusion can specify an operating mode, a time period, an amount of fluid to be delivered, and/or a variety of other data regarding the infusion. When the infusion is not a pulse mode infusion (412), the velocity of the pump can be controlled (414) using, for example a velocity motion control algorithm. The processor 210 of the infusion pump can determine whether the pulse mode should be activated based on a specified type or a specified fluid infusion rate of an infusion treatment. The type and/or infusion rate may be manually programmed into the infusion pump using a user interface, such as a touchscreen. Alternatively, the type and/or infusion rate may be received via the communication interfaces 230 via an electronic prescription.

When the infusion is a pulse mode infusion (412), a pulse volume for each pulse can be determined (416), a pulse cycle time can be determined (418), and a pulse mode flow can be started (420). The pulse volume and/or pulse cycle time can be determined based on the volume of fluid to be delivered and/or the time period associated with the infusion. Position motion control can be executed (422) to perform a delay and a pulse. When the infusion process is complete (424), the infusion can be stopped (426). The infusion process can be indicated as completed based on a variety of criteria such as, but not limited to, determining if the designated time has elapsed, the specified movements (e.g., number of revolutions) of the motor and/or pump have been completed, and/or specified number of pulses of fluid has been delivered. The pulse movement can be monitored and determined to be correct (428). When the pulse movement is correct (428), the process 400 can proceed to block 422. When the pulse movement is not correct (428), the operation of the motor can be adjusted (430) and the process 400 can proceed to block 422. A variety of processes for controlling the operation of a motor and pump are described in more detail with respect to FIG. 5.

Figure 5:
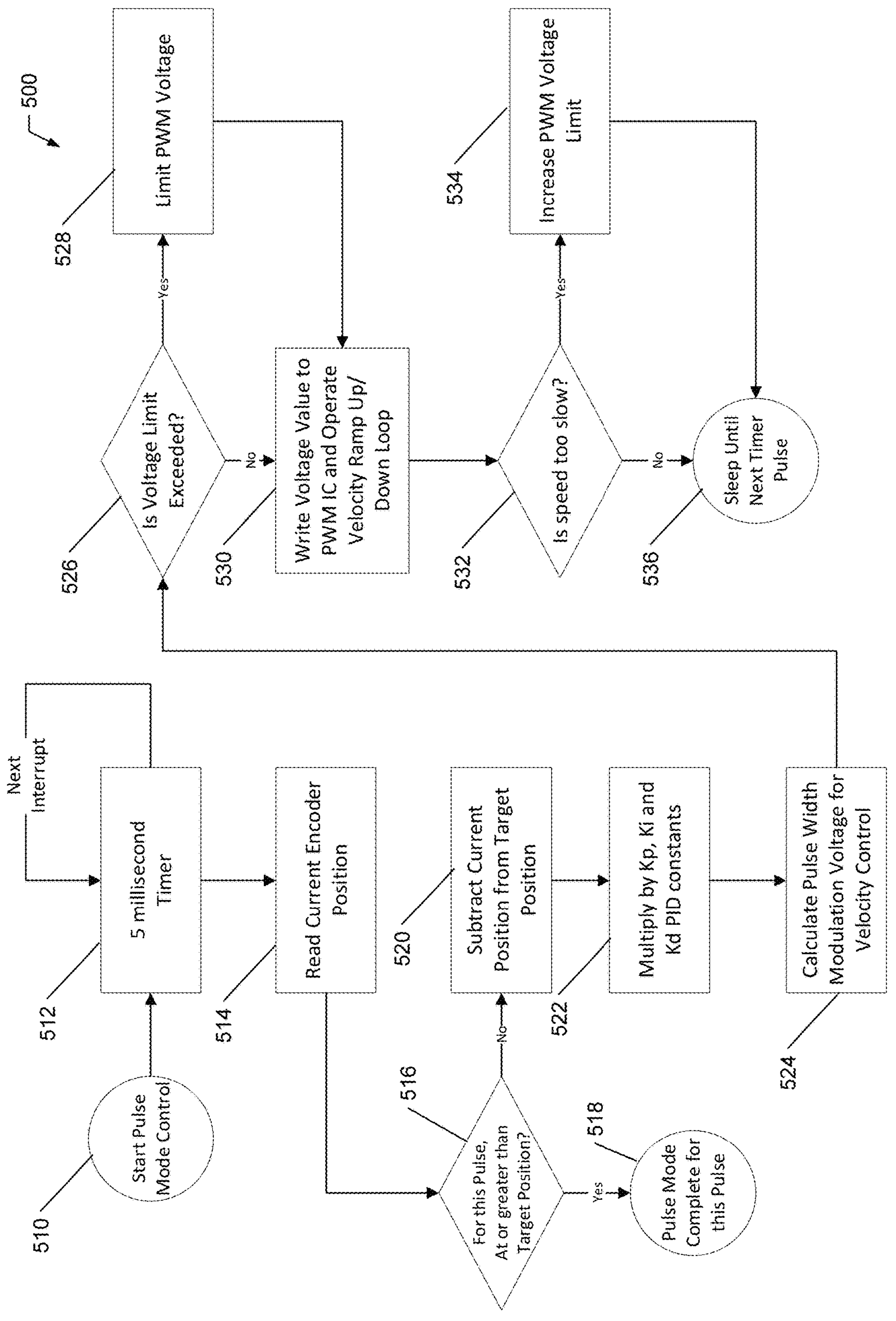
FIG. 5 illustrates a flowchart of a positional control process, according to an example aspect of the present disclosure.

FIG. 5 illustrates a flowchart of a positional control process 500, according to an example aspect of the present disclosure. Although the process 500 is described with reference to the flowchart illustrated in FIG. 5, it should be appreciated that many other methods of performing the acts associated with the process 500 may be used. For example, the order of some of the blocks may be changed, certain blocks may be combined with other blocks, one or more blocks may be repeated, and some of the blocks described are optional. The process 500 may be performed by processing logic that may include hardware (circuitry, dedicated logic, etc.), software, or a combination of both. In a variety of aspects, positional control processes can be performed by a controller operating a motor and/or pump within an infusion pump device.

A pulse mode control process can be started (510) by the processor 210 and/or the PID controller 300 and a startup timer can elapse (512). An encoder position can then be read (514) by the PID controller 300. When the encoder position is at the target position or greater than the target position (516), the pulse mode process can complete (518). When the encoder position is not at the target position or not greater than the target position (516), the current position can be subtracted (520) from the target position and the difference can be modified (522) based on the PID operating parameters (e.g. $K_p$, $K_i$, and $K_d$) for the controller. A voltage can be calculated (524). The voltage can be used to control the velocity of the fluid being pumped. Increasing the voltage can increase the amount of fluid being pumped per pulse. The voltage can be any voltage, such as a pulse width modulation (PWM) voltage, utilized by a device in accordance with aspects of the disclosure. When a voltage limit is exceeded (526), the voltage can be limited (528). In this way, the device can be operated within the operating limits of the device. A motor can be programmed (530) to operate at the calculated voltage and the motor can be operated. When the operation of the motor is too slow or below a threshold (532), the voltage limit can be increased (534) and the process can proceed to block 536. When the operation speed is not too slow (532), the process can proceed to block 536. The process can sleep (536) until the next pulse.

Figure 6:
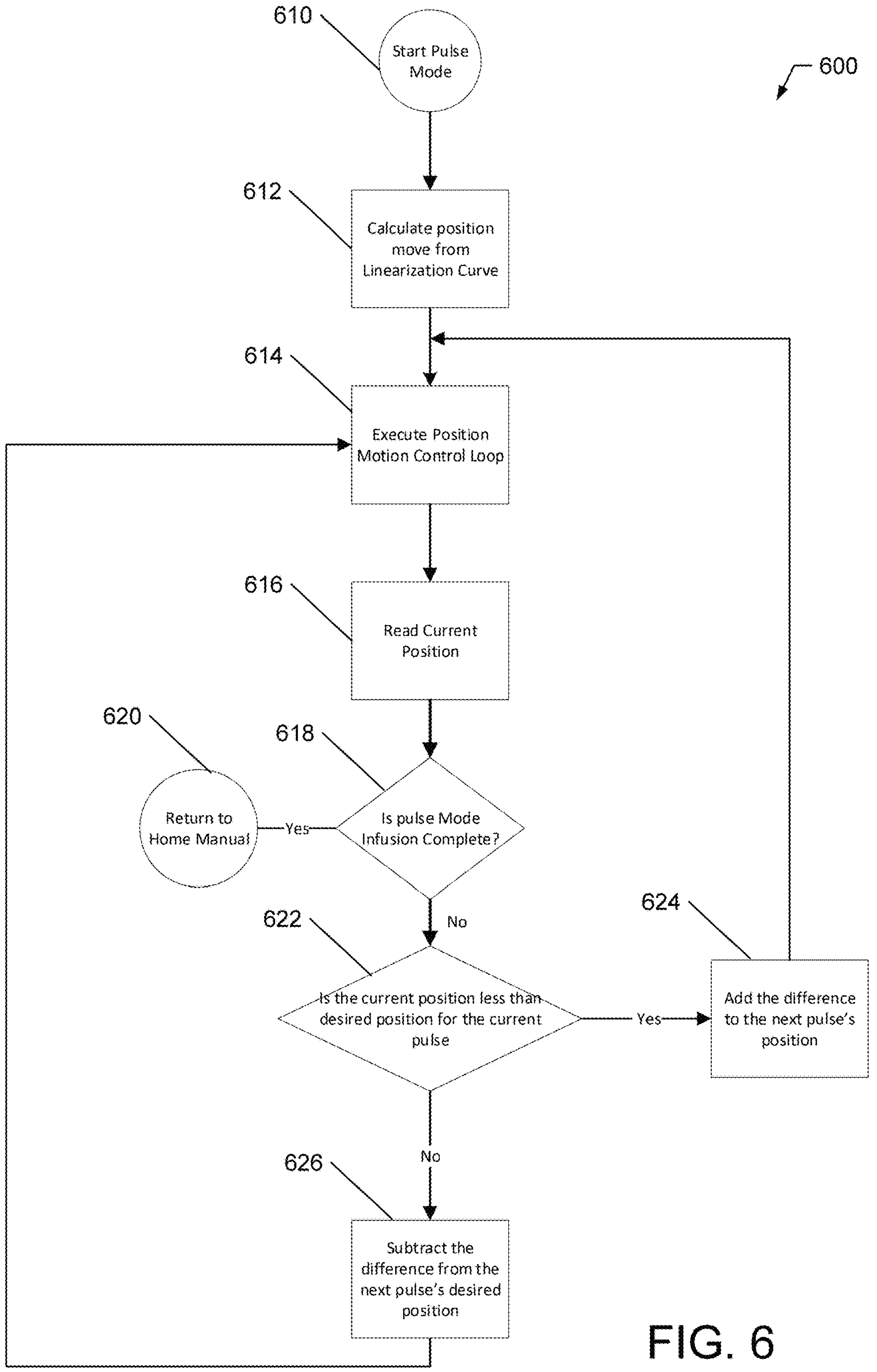
FIG. 6 illustrates a flowchart of an accumulated error compensation process, according to an example aspect of the present disclosure.

FIG. 6 illustrates a flowchart of an accumulated error compensation process 600, according to an example aspect of the present disclosure. The accumulated error compensation process 600 may be performed after pulse has been completed. Although the process 600 is described with reference to the flowchart illustrated in FIG. 6, it should be appreciated that many other methods of performing the acts associated with the process 600 may be used. For example, the order of some of the blocks may be changed, certain blocks may be combined with other blocks, one or more blocks may be repeated, and some of the blocks described are optional. The process 600 may be performed by processing logic that may include hardware (circuitry, dedicated logic, etc.), software, or a combination of both. In a variety of aspects, accumulated error compensation processes can be performed by a controller operating a motor and/or pump within an infusion pump device.

A pulse mode can be started (610). A position move can be calculated (612). In many aspects, the position move is calculated based on a linearization curve. A position motion control loop can be executed (614). A current position of a motor encoder can be read (616). When the pulse mode infusion is complete (618), the process can end (620). When the pulse mode infusion is not complete (618), the difference between the current position and the desired (target) position of the encoder can be determined. When the current position is less than the desired position for the current pulse (622), the difference can be added (624) to the next pulse's position and the process can return to block 614. For example, a delay before the next pulse begins can be shortened based on a value of the difference. When the current position is not less than the desired position for the current pulse (622), the difference can be subtracted (626) from the next pulse's position and the process can return to block 614. For example, a delay before the next pulse begins can be lengthened based on a value of the difference.

Figure 7A:
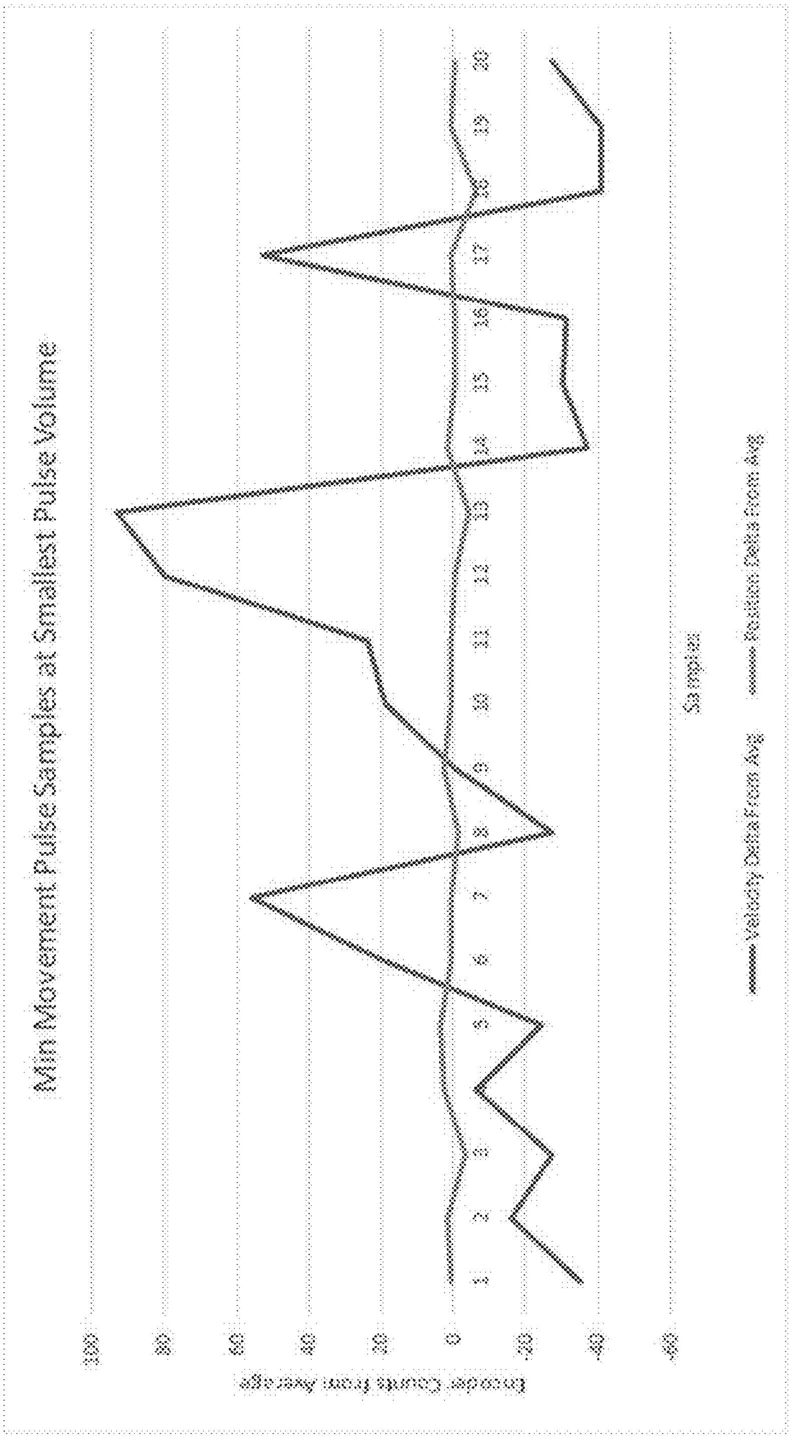
FIGS. 7A-C illustrate positional control accuracy for a motor according to example aspects of the present disclosure.
Figure 7B:
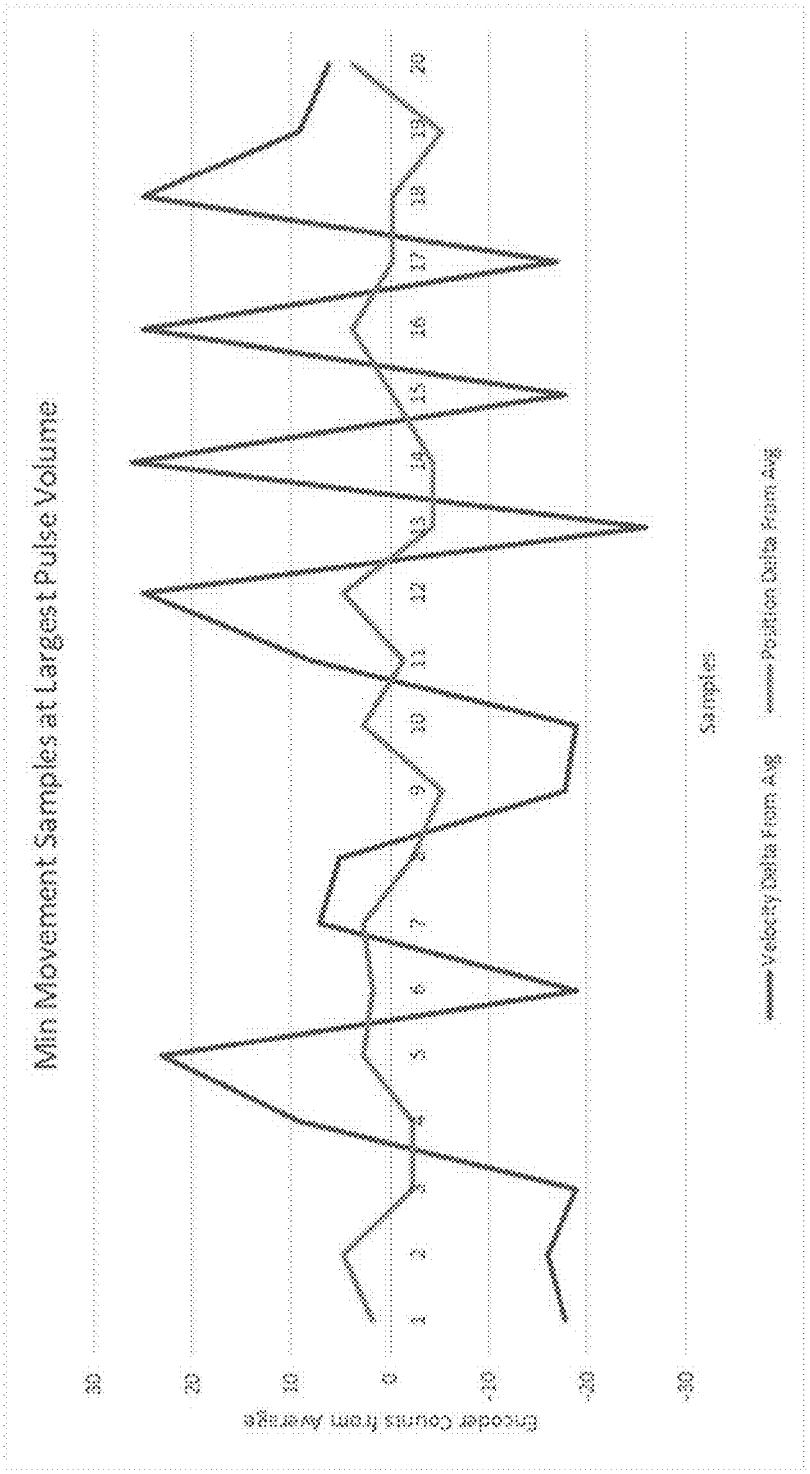
Figure 7C:
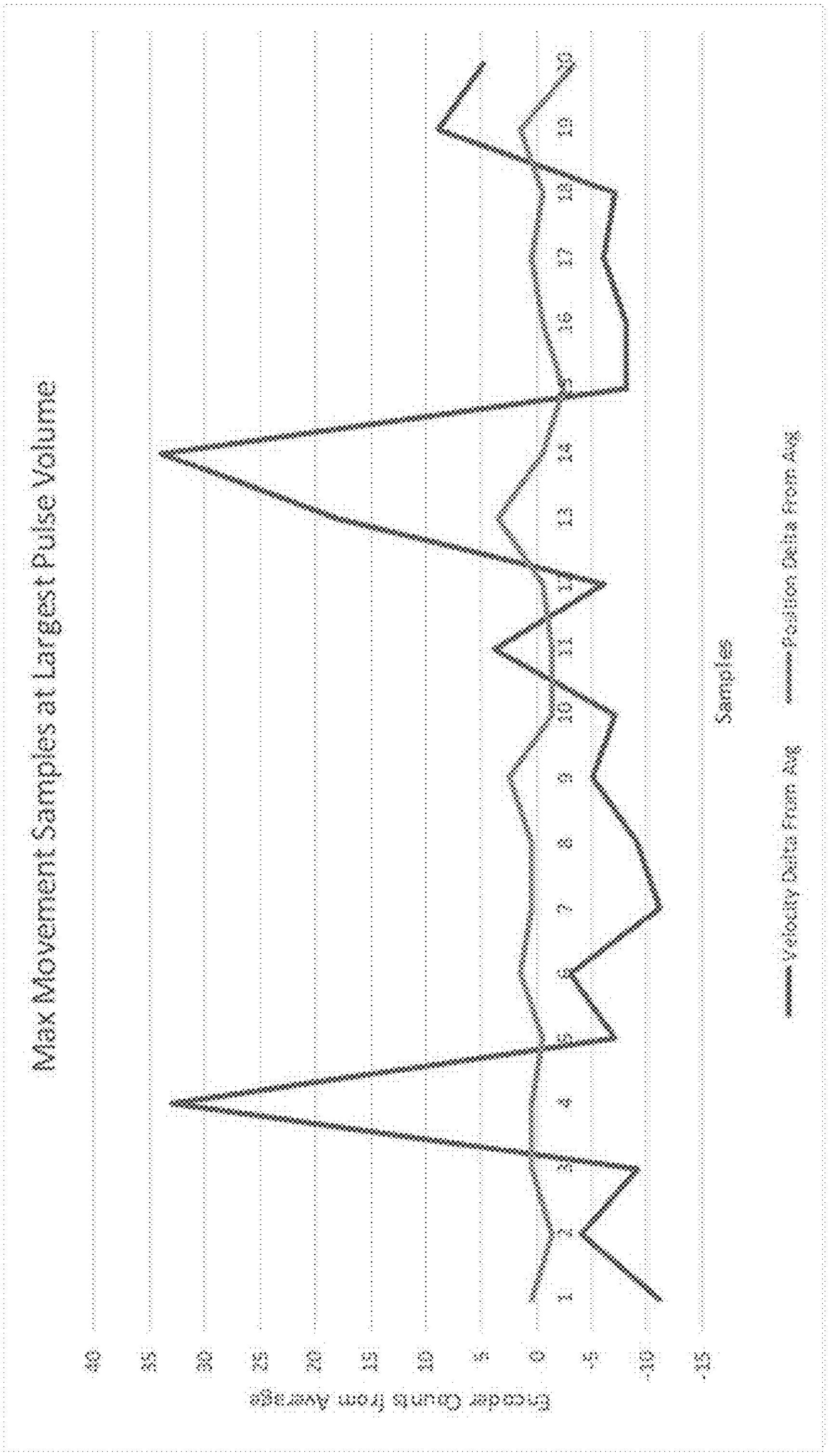

FIGS. 7A-C illustrate positional control accuracy for a motor, according to example aspects of the present disclosure. As shown in FIG. 7A, a graph 700 illustrates pulses with a minimum motor movement for a smallest pulse volume, in accordance with aspects of the present disclosure. As shown in FIG. 7B, a graph 720 illustrates pulses with the minimum motor movement for a largest pulse volume, in accordance with aspects of the present disclosure. As shown in FIG. 7C, a graph 740 illustrates pulses with the maximum motor movement for a largest pulse volume in accordance with aspects of the present disclosure. As can be seen from FIGS. 7A-C, position control methods in accordance with aspects of the disclosure provide consistent motor movement, ensuring accurate fluid delivery particularly as compared to velocity control methods.

As described herein, controllers can be used for pulse mode motor movements. In several aspects, motor speed can be controlled such that the pulse speed is slow enough to be safe for a patient and a pump mechanism. In addition, the pulse speed is fast enough such that battery life concerns are meet and the motor has head room to allow continued movement even under higher torque scenarios. The motor speed is ramped up to limit current spikes as the motor gets up to speed. In order to achieve these goals, a floating motor voltage percentage limit can be used.

Figure 8A:
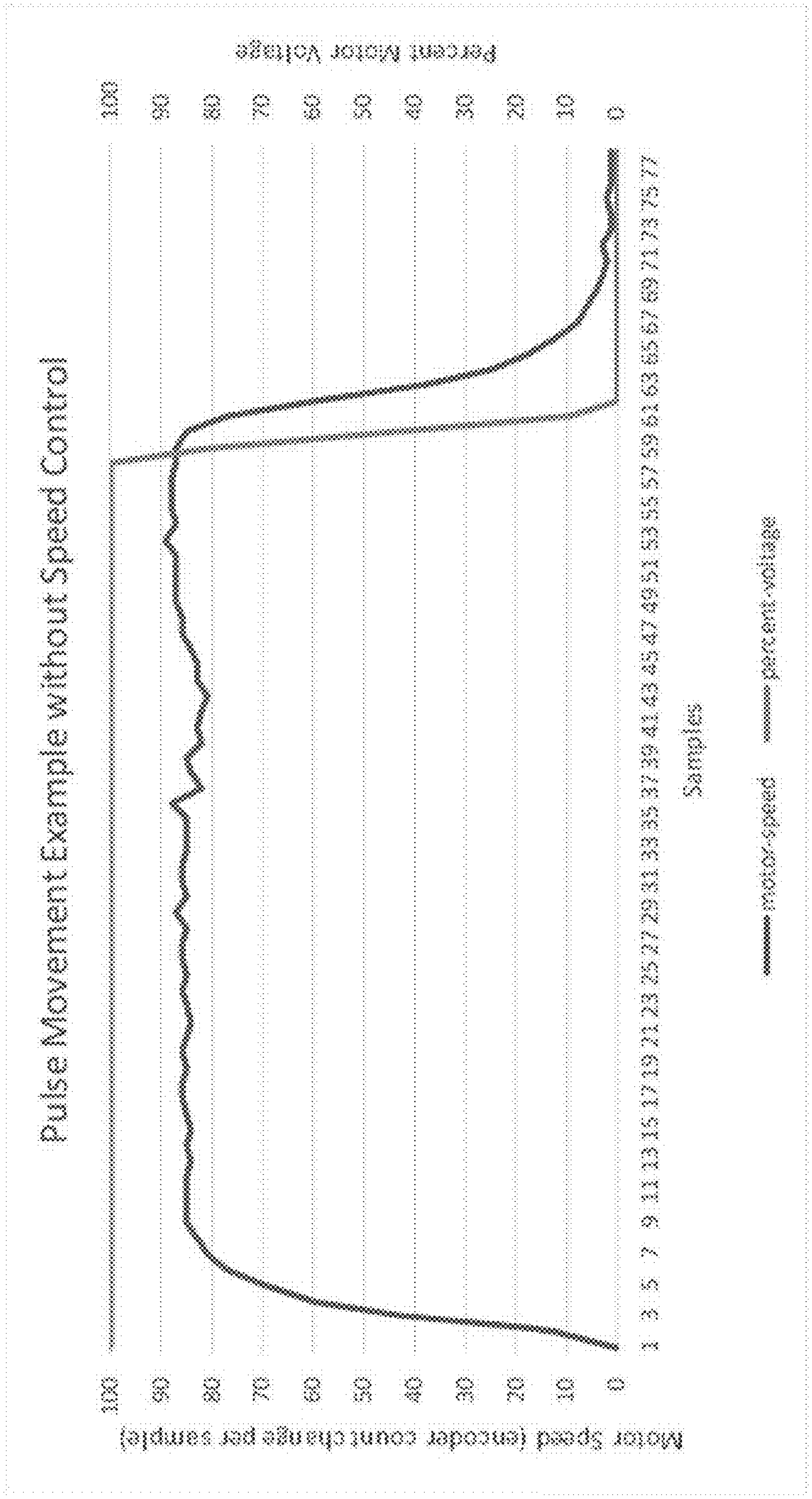
FIGS. 8A-B illustrate velocity control during motor movements, according to example aspects of the present disclosure.
Figure 8B:
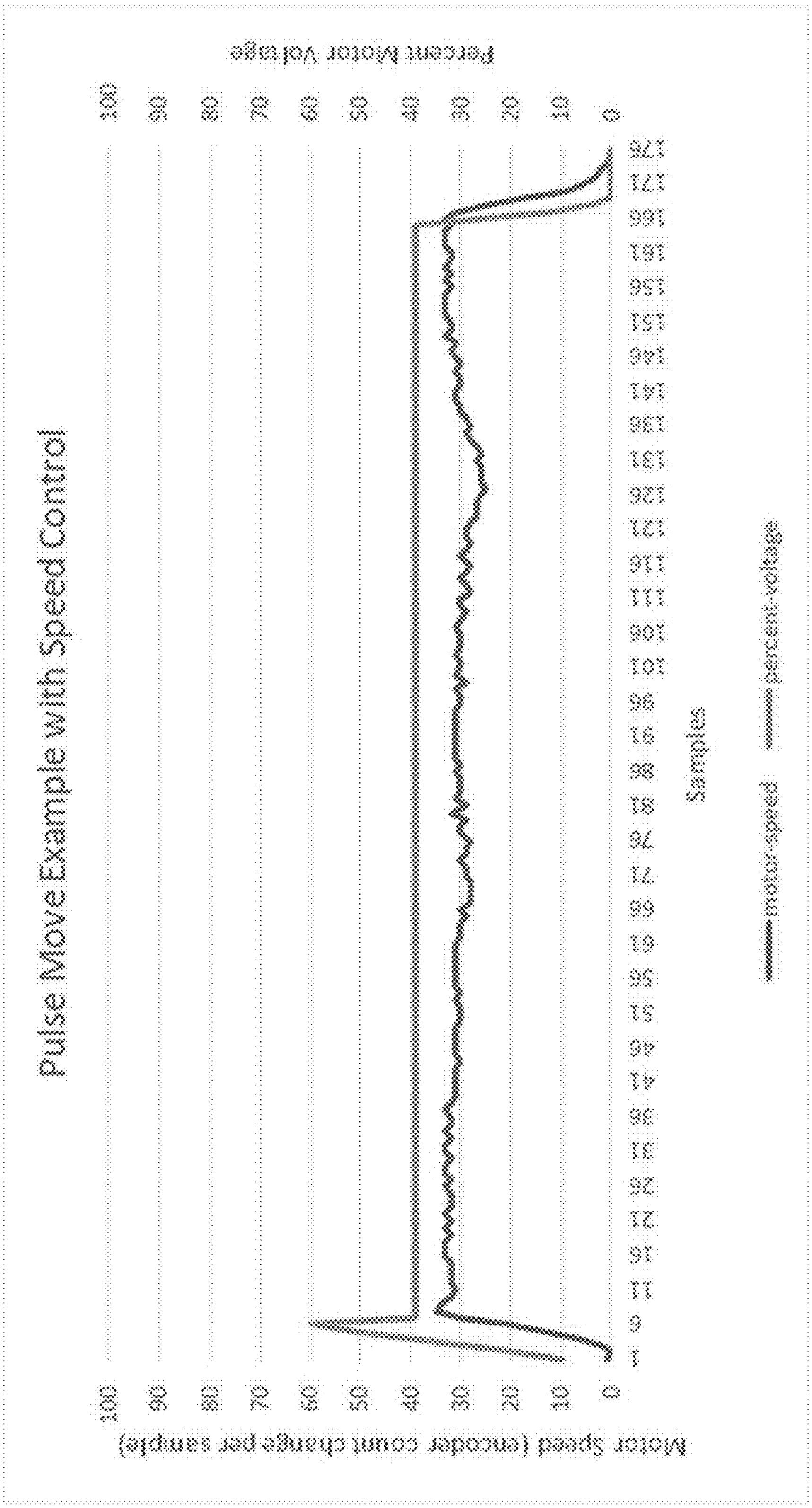

FIGS. 8A-B illustrate velocity control during motor movements and the effect of this limit on the motor voltage and speed, according to example aspects of the present disclosure. As shown in FIG. 8A, a graph 800 illustrates the motor voltage being directly controlled by the PID controller with the only limit on the motor voltage being the 100% voltage limit. In this example, the motor voltage is driven at 100% for most of the movement. The motor voltage drops only as the movement reaches the target. The motor speed, as shown via the change in the encoder counts per sample, reaches the mechanism limit and drops off as the motor voltage drops.

As shown in FIG. 8B, a graph 820 illustrates that the motor voltage is ramped up to avoid current spikes. When the motor reaches the desired speed, the floating motor voltage limit is applied. In this example, this floating voltage limit does not need to be further adjusted from the default since the speed stays relatively constant during the movement. The motor voltage drops off at the end of the movement similar to the case without speed control such that the controller can naturally drop the voltage as the movement nears its target. It should be noted that there are trade-offs between time and movement speed depending on the operating mode of the infusion pump. These factors can be taken into account to determine the desired speed and the processes described herein allow those choices to be made with fewer downsides.

As described herein, controllers measure and compensate for pulse movement errors accumulating during the operation of a motor and/or pump. If uncorrected, these cumulative errors can result in large movement errors over the entire infusion period. As described herein, the controller is configured to prevent these accumulation errors by compensating for a previous pulse error into the movement of a next pulse. If a pulse overshot the end position, then that overshoot amount is correspondingly removed from the next pulse movement request. Similarly, if a pulse undershot the end position, then that undershoot amount would be added to the next pulse movement request.

Figure 9A:
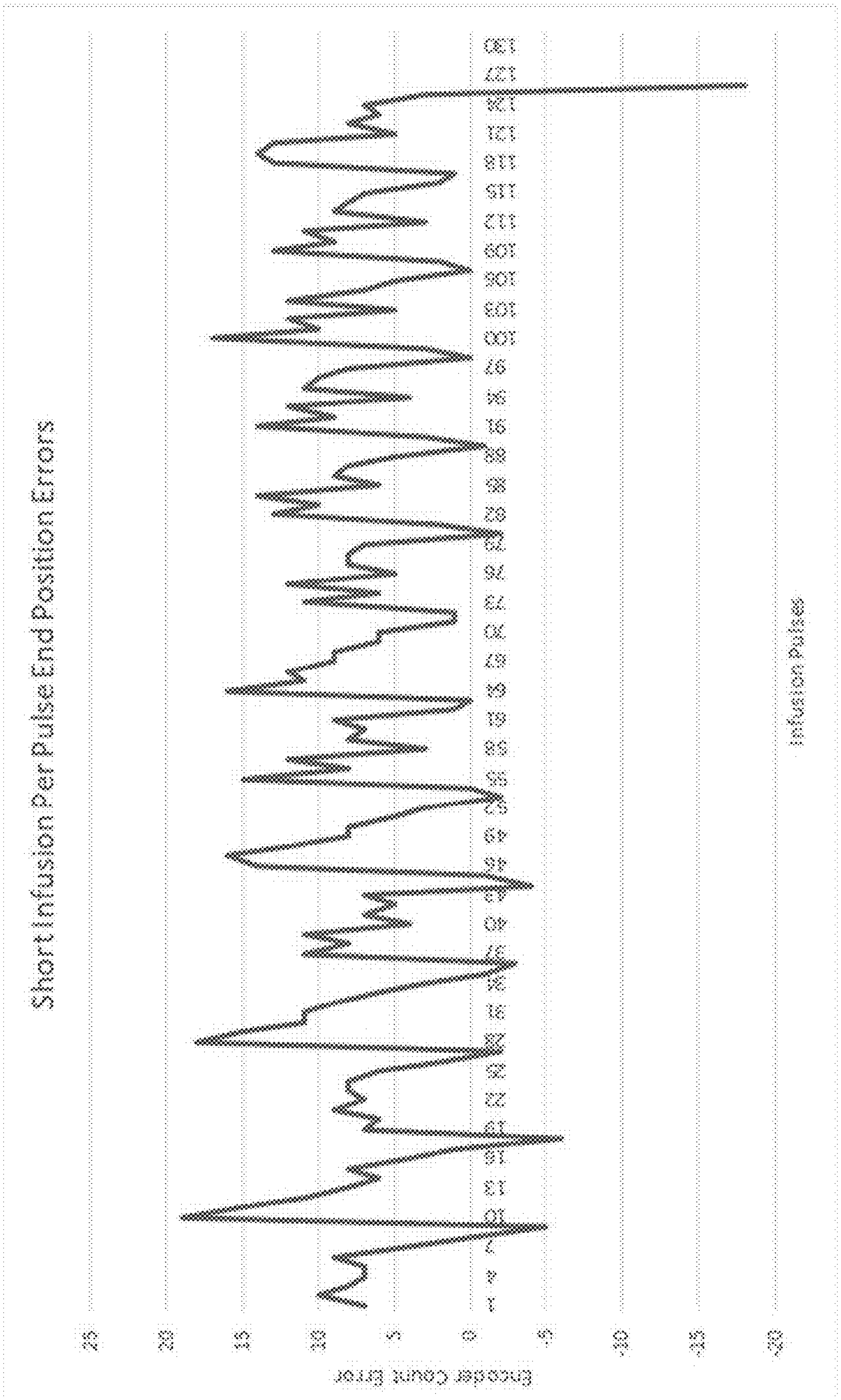
FIGS. 9A-C illustrate error compensations, according to example aspects of the present disclosure.
Figure 9B:
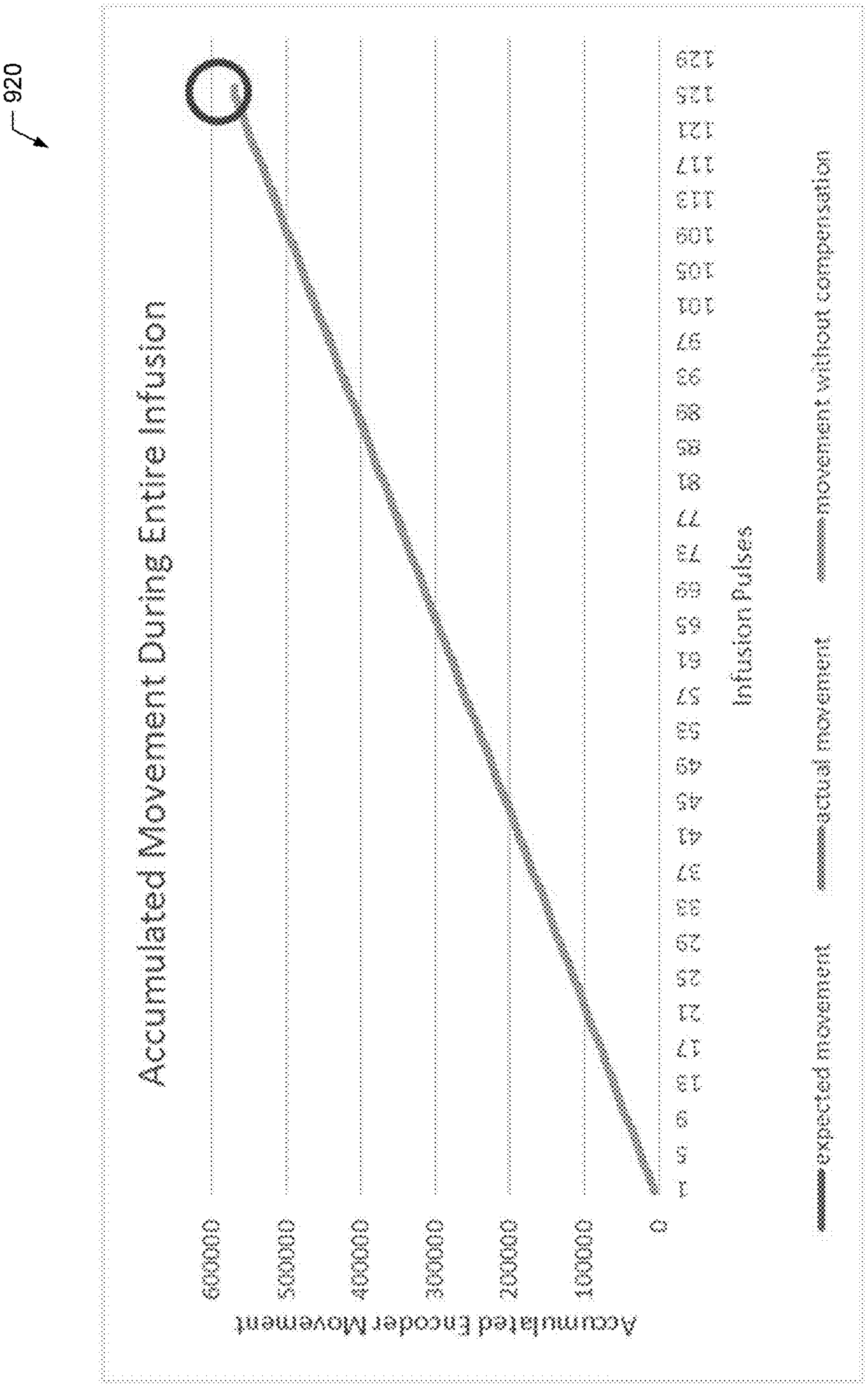
Figure 9C:
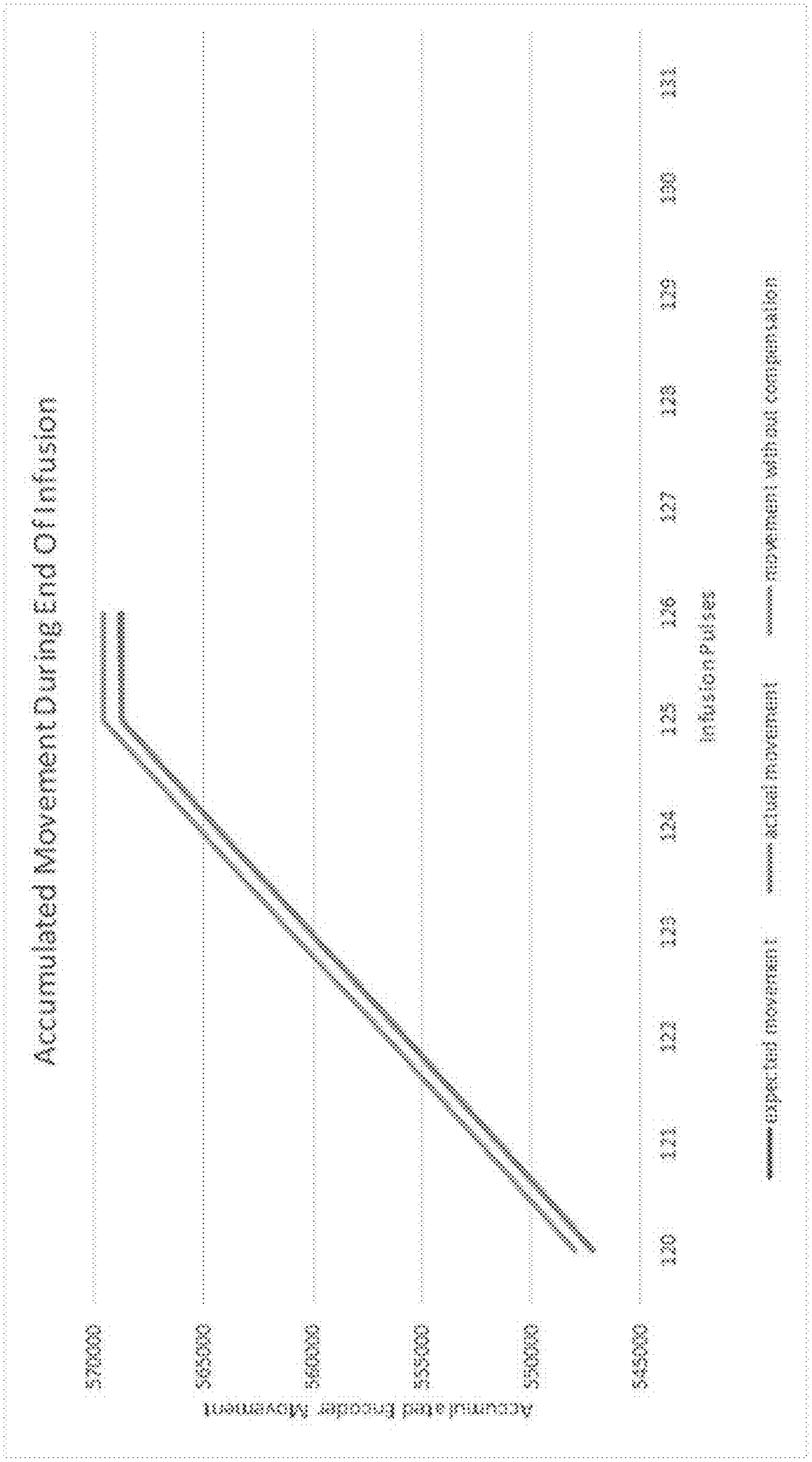

FIGS. 9A-C illustrate error compensations according to example aspects of the present disclosure. As shown in FIG. 9A, a graph 900 illustrates the per pulse error in this operating mode. In graph 900, a short infusion (<5 minutes) at the highest pulse mode flow rate is shown. During this infusion, due to the higher speed, the pulses tended to overshoot the end position slightly. The last pulse was a very short movement that tends to undershoot. The sum of the position error is +858 encoder counts, which is nearly one quarter of a motor revolution of error. As shown in FIG. 9B, a graph 920 illustrates the accumulated encoder movement for the entire infusion period with three sets of data: the expected movement, the actual movement (with sequential pulse compensation), and what the movement would have been without sequential pulse compensation. As shown in FIG. 9C, a graph 940 illustrates the portion of the movement without sequential pulse compensation as highlighted in graph 920. As illustrated in the graph 940, the expected and actual movement data are similar until the last sample, where the final pulse error can be seen as the error is larger than the previous errors.

It should be appreciated that all of the disclosed methods and procedures described herein can be implemented using one or more computer programs, components, and/or program modules. These components may be provided as a series of computer instructions on any conventional computer readable medium or machine-readable medium, including volatile or non-volatile memory, such as RAM, ROM, flash memory, magnetic or optical disks, optical memory, or other storage media. The instructions may be provided as software or firmware and/or may be implemented in whole or in part in hardware components such as ASICs, FPGAs, DSPs, or any other similar devices. The instructions may be configured to be executed by one or more processors, which when executing the series of computer instructions, performs or facilitates the performance of all or part of the disclosed methods and procedures. As should be appreciated by one of skill in the art, the functionality of the program modules may be combined or distributed as desired in various aspects of the disclosure.

Although the present disclosure has been described in certain specific aspects, many additional modifications and variations would be apparent to those skilled in the art. In particular, any of the various processes described above can be performed in alternative sequences and/or in parallel (on the same or on different computing devices) in order to achieve similar results in a manner that is more appropriate to the requirements of a specific application. It is therefore to be understood that the present disclosure can be practiced otherwise than specifically described without departing from the scope and spirit of the present disclosure. Thus, embodiments of the present disclosure should be considered in all respects as illustrative and not restrictive. It will be evident to the annotator skilled in the art to freely combine several or all of the embodiments discussed here as deemed suitable for a specific application of the disclosure. Throughout this disclosure, terms like "advantageous", "exemplary" or "preferred" indicate elements or dimensions which are particularly suitable (but not essential) to the disclosure or an embodiment thereof, and may be modified wherever deemed suitable by the skilled annotator, except where expressly required. Accordingly, the scope of the invention should be determined not by the embodiments illustrated, but by the appended claims and their equivalents.

What is claimed is:

1. A computer-implemented method for performing an infusion treatment, the method comprising:
- dispensing, by a pump controlled by a controller, a fluid from a fluid supply in a pulse mode over a period, the period comprising a plurality of pulses, by:
  - determining a pulse volume for a pulse,
  - determining a pulse cycle time, and
  - for the period:
    - controlling a position of the pump to:
      - perform a delay, and
      - perform a pulse to dispense an amount of the fluid, the pulse performed for the pulse cycle time,
    - calculating an overshoot or undershoot of the amount of the fluid dispensed relative to the pulse volume,
    - adjusting the pulse cycle time, for at least the next pulse in the period, based on the calculated overshoot or undershoot, and
    - repeating the dispensing until the period has elapsed, and
  - controlling a voltage level of the pulse by:
    - starting, via the controller, a timer;
    - after an elapsed time, reading via the controller, an encoder position of a pump motor,
    - comparing via the controller, the encoder position of the pump motor to a target position,
    - when the encoder position is equal to or greater than the target position, maintaining, via the controller, a voltage level of at least the next pulse in the period, and
    - when the encoder position is less than the target position, subtracting, via the controller, the encoder position from the target position and using the difference to increase the voltage level of at least the next pulse in the period.

2. The computer-implemented method of claim 1, wherein the fluid supply comprises an IV bag.

3. The computer-implemented method of claim 1, wherein the overshoot or undershoot is calculated based on measuring the position of the pump prior to and after the pulse.

4. The computer-implemented method of claim 1, wherein the voltage level of the pulse is increased by:
- adjusting, via the controller, the difference between the encoder position and the target position using at least one PID operating parameter;
- calculating, via the controller, a pulse width modulation (PWM) voltage using the adjusted difference; and
- increasing, via the controller, the voltage level of at least the next pulse in the period based on the calculated PWM voltage.

5. The computer-implemented method of claim 4, wherein the at least one PID operating parameter includes $K_p$, $K_i$, and $K_d$ for the controller.

6. The computer-implemented method of claim 4, further comprising:
- comparing, via the controller, the PWM voltage to a voltage limit; and
- when the voltage limit is exceeded, reducing, via the controller, the PWM voltage to the voltage limit.

7. The computer-implemented method of claim 4, further comprising:
- comparing, via the controller, the PWM voltage to a minimum motor speed; and when the minimum motor speed is below a threshold, increasing, via the controller, the PWM voltage or the voltage limit to at least the threshold.

8. The computer-implemented method of claim 1, wherein the pulse volume for the pulse is determined based on a volume of the fluid to be delivered.

9. The computer-implemented method of claim 1, wherein the pulse cycle time is determined based on at least one of a volume of the fluid to be delivered or a time period associated with the infusion treatment.

10. The computer-implemented method of claim 1, further comprising after the period:

reading, via the controller, an encoder position of a motor of the pump;

comparing, via the controller, the encoder position of the motor to a target position;

when the encoder position is greater than the target position, subtracting, via the controller, a difference between the target position and the encoder position from a position of a next pulse for a next period; and when the encoder position is less than the target position, adding, via the controller a difference between the encoder position and the target position to a position of a next pulse for a next period.

11. An infusion pump apparatus comprising:

a pump motor configured to pump fluid through intravenous tubing; and a controller configured to control the pump motor to perform an infusion treatment, the controller being configured to:

cause the fluid to be dispensed in a pulse mode over a period, the period comprising a plurality of pulses, by:

determining a pulse volume for a pulse, determining a pulse cycle time, and for the period:

controlling a position of the pump motor to:

perform a delay, and perform a pulse to dispense an amount of the fluid, the pulse performed for the pulse cycle time, calculating an overshoot or undershoot of the amount of the fluid dispensed relative to the pulse volume, adjusting the pulse cycle time, for at least the next pulse in the period, based on the calculated overshoot or undershoot, and repeating the dispensing until the period has elapsed, and control a voltage level of the pulse by:

starting a timer, after an elapsed time, reading an encoder position of the pump motor, comparing the encoder position of the pump motor to a target position, when the encoder position is equal to or greater than the target position, maintain a voltage level of at least the next pulse in the period, and when the encoder position is less than the target position, subtracting, the encoder position from the target position and use the difference to increase the voltage level of at least the next pulse in the period.

12. The apparatus of claim 11, wherein the controller comprises a proportional, integral, derivative (PID) controller.

13. The apparatus of claim 11, wherein the overshoot or undershoot is calculated based on measuring the position of the pump motor prior to and after the pulse.

14. The apparatus of claim 11, wherein the controller increases the voltage level of the pulse by:

adjusting the difference between the encoder position and the target position using at least one PID operating parameter;

calculating a pulse width modulation (PWM) voltage using the adjusted difference; and increasing the voltage level of at least the next pulse in the period based on the calculated PWM voltage.

15. The apparatus of claim 14, wherein the at least one PID operating parameter includes $K_p$, $K_i$, and $K_d$ for the controller.

16. The apparatus of claim 14, wherein the controller is further configured to:

compare the PWM voltage to a voltage limit; and when the voltage limit is exceeded, reduce the PWM voltage to the voltage limit.

17. The apparatus of claim 11, wherein the controller is configured to enter the pulse mode based on a specified type or a specified fluid infusion rate of the infusion treatment.

18. The apparatus of claim 11, wherein the controller is further configured to after the pulse, read an encoder position of the pump motor;

compare the encoder position of the pump motor to a target position;

when the encoder position is greater than the target position, subtract a difference between the target position and the encoder position from a position of a next pulse for a next period; and when the encoder position is less than the target position, add a difference between the encoder position and the target position to a position of a next pulse for a next period.

* * * * *